United States Patent [19] [11] 4,042,463
Haque et al. [45] Aug. 16, 1977

[54] METHOD OF SIMULTANEOUSLY CULTIVATING MULTIPLE COLONIES OF MICROORGANISMS

[75] Inventors: Riaz-ul Haque, Glen Ellyn; Richard A. Murphy, Oak Park, both of Ill.

[73] Assignee: International Foundation of Microbiology, Chicago, Ill.

[21] Appl. No.: 598,754

[22] Filed: July 25, 1975

Related U.S. Application Data

[60] Continuation of Ser. No. 233,023, March 9, 1972, abandoned, which is a division of Ser. No. 412,479, Nov. 2, 1973, Pat. No. 3,912,596.

[51] Int. Cl.² ............................................. C12B 1/02
[52] U.S. Cl. ..................................... 195/120; 195/108
[58] Field of Search ........................ 195/108, 120, 139

[56] References Cited

U.S. PATENT DOCUMENTS 2,874,091  2/1959  Fisk ........................................ 195/139

Primary Examiner—Alvin E. Tanenholtz
Attorney, Agent, or Firm—John L. Parker

[57] ABSTRACT

A multiple inoculation system is provided for the transfer, cultivation, maintenance and identification of microorganisms. The system includes a multiple needle inoculating plate, a separate plate including multiple wells corresponding to the needles for holding inoculum and transferring it to the needles, and a culture dish having a plurality of compartments interconnected with each other in the central portion of the dish. The culture dish is filled with a suitable solidifiable liquid culture medium by pouring the medium onto the central or any portion of the dish so that the medium readily flows into each of the compartments. After the culture medium has solidified, the compartments remain separated from one another so that after the medium is cultivated the spreading of microorganisms between compartments is minimized and mutual interference in test reactions is avoided.

2 Claims, 3 Drawing Figures

4,042,463

METHOD OF SIMULTANEOUSLY CULTIVATING MULTIPLE COLONIES OF MICROORGANISMS

DESCRIPTION OF THE INVENTION

This is a continuation of our application Ser. No. 233,023 filed Mar. 9, 1972, now abandoned and a division of our application Ser. No. 412,479 filed Nov. 2, 1973 now U.S. Pat. No. 3,912,596.

The present invention relates to an inoculating system for identifying microorganisms, and particulary to such a system for achieving simultaneous inoculation of multiple samples.

For many years, an inoculating loop, inoculating needle, test tubes, and Pertri plates were the only tools available to the microbiologist involved in the identification of microorganisms. He began his work by spreading (streaking) the sample, using the inoculating loop, onto a solid agar culture medium contained in a Petri dish. The dish was then incubated, and the isolated colonies of organisms which generally appeared after 12-24 hours of incubation were picked-up with the incoulating needle and transferred to an agar slant (an agar medium which had been allowed to solidify in a tube in a slanted condition). The resulting slant culture was regarded as the stock culture and was subjected to further tests to determine the indentification of the disease producing or other microorganisms.

In recent years, various multiple inoculation techniques have been used for allowing the simultaneous inoculation of several cultures onto a single substrate, thereby permitting more rapid identification of the microorganisms. Multiple inoculation techniques have been used with cultures of fungi, yeasts, bacteria, and various other organisms. The tests generally involve the determination of the biochemical activities of the culture, such as the ability to use certain sugars, hydrolyse proteins, polysaccharides, fats, and nucleic acids and the ability to produce certain intermediary or end products such as indole, acetylmethyl carbinol, acid, or acids and gas. Multiple inoculation is much less tedious and time consuming than the sequential inoculation of individual cultures previously carried out by hand.

We previously described a multiple inoculating device in *The American Journal of Clinical Pathology,* Vol. 47, No. 4, p. 554 (1967) in which a plate carrying multiple inoculating needles is used with an agar culturing dish. In one form, the plate carrying the needles is pressed onto the surface of the agar to create slight depressions in the agar corresponding to the imprint of the needles, and bacteria from isolated colonies is then inoculated into each of the multiple depressions using the standard inoculation needle or loop. After incubation of the agar substrate, the multiple inoculator is sterilized, re-pressed into the agar, and then pressed into ten or more replicate test plates.

In another form which we described, an additional plate is utilized containing multiple wells corresponding to each of the needles carried by the inoculating plate. Colonies of organisms are placed in the wells, and organism transfer to the inoculating needles is achieved by lowering the needle carrying plate over the wells until the needles are in contact with and pick up the respective organisms carried in the wells. Then, multiple inoculation is achieved by contacting the plate carrying the needles with the agar substrate. A similar arrangement is described in U.S. Pat. No. 2,956,931 to Goldberg.

Other descriptions of devices for multipoint inoculation of agar plates are also found in the literature. But these techniques and devices suffer the serious disadvantage that diffusion of organisms often takes place through the agar substrate or other culture medium, and sometimes organism colonies spread along the surface of the agar. Such migration of different organisms into one another may impair or completely nullify the results of the identification test reactions.

As might be expected, the prior art has tried to overcome these problems in various ways but with only limited success. For example, one technique that has been utilized with multipoint inoculators is the so-called "divided Petri dish" (*Journal of Applied Bacteriology,* Vol. 30, p. 495 (1967) by Sneath et al.) in which the culture media is placed in a multi-compartment Petri dish which looks much like an ice tray. Each compartment in the tray is completely separated from the next, and corresponds to a particular prong or needle on the multipoint inoculating plate. While such compartmented tray devices manage to prevent overgrowth and spreading of organisms as well as mutual interference in test reactions, the step of filling each of the compartments with agar or other culture media is found to be unduly time consuming. Each individual compartment must be separately filled, usually one at a time. It can take as long as 5 or 10 minutes to fill a tray having 20-30 compartments, a situation which significantly limits the productivity of the modern day microbiology laboratory.

It is an object of the present invention to provide a multiple inoculation system for the transfer, cultivation, maintenance and identification of microorganisms which eliminates cumbersome and tedious multiple manipulations required by prior practices. A related object is to provide such a multiple inoculation system in which a laboratory technician may carry out many microorganism identification tests simultaneously in less time than heretofore required. Still another related object is to provide such a multiple inoculation system in which the culture media may be quickly and easily prepared for simultaneous cultivation of multiple test samples without the need for specially trained laboratory personnel.

Another object of the invention is to provide a technique and devices for multiple inoculation of culture media in which the media may be speedily and simply prepared for cultivation of multiple test samples and yet in which positive separation of the individual test samples from one another is assured. Yet another object is to provide such a multiple inoculation system in which multiple test samples of culture media may be rapidly and simultaneously cultivated with assurance that neither the microorganisms contained in adjacent samples nor their reaction products with the culture media will migrate or otherwise intersperse into each other. An ancillary object is to provide such a multiple inoculation system in which positive, non-interfering test results may be achieved in minimum time.

Other objects and advantages of the present invention will become apparent upon reading the following detailed description and upon reference to the drawings, in which FIG. 1 is a bottom plan view of an illustrative inoculation plate which may be used in carrying out the invention, showing a typical arrangement of inoculating needles on the plate.

While the invention is described in connection with certain preferred embodiments, it will be understood that we do not intend to limit the invention to those embodiments. On the contrary, we intend to cover all alternatives, modifications and equivalents as may be included within the spirit and scope of the invention as defined by the appended claims.

Figure 1:
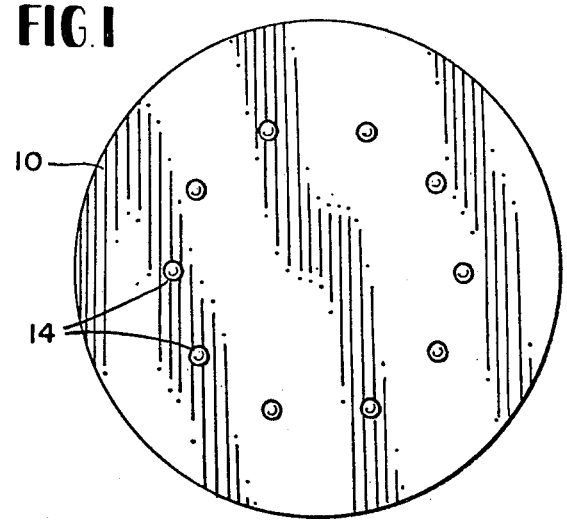
Figure 2:
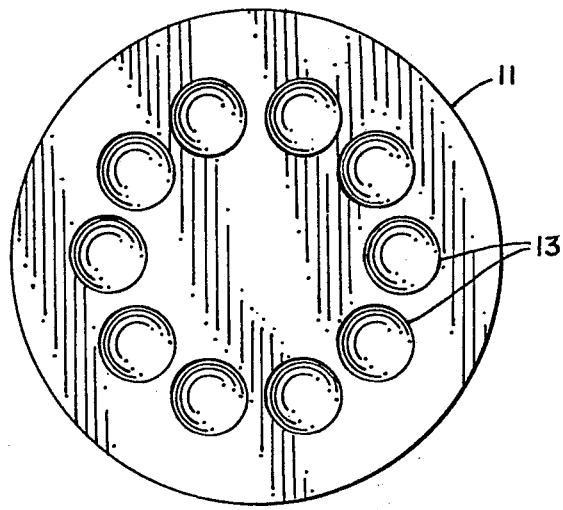
FIG. 2 is a top plan view of an illustrative holding plate for the inoculum, showing typical arrangement of wells on the plate for holding the inoculum.
Figure 3:
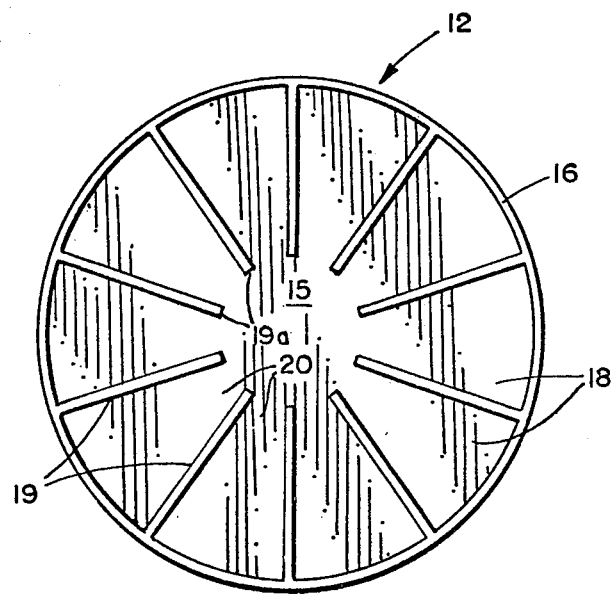
FIG. 3 is a top plan view of an illustrative culture dish suitable for use in carrying out the invention.

Turning now to the drawings, a three component system for the multiple inoculation and cultivation of microorganisms is shown. The system includes a plate or other device 10 for inoculation (FIG. 1), a separate plate or similar device 11 for preparing and holding inoculum to be used (FIG. 2), and a culture dish or other device 12 for culturing the inoculum (FIG. 3).

In the form shown in the drawings, the inoculation means 10 takes the form of a flat circular plate or disc carrying a plurality of depending inoculating needles or pins 14 arranged in spaced apart circular relationship around the plate. As illustrated, ten needles 14 are utilized, although the number of needles may be varied as desired. The inoculation plate 10 may also, if desired, include one or more guides (not shown) for aligning and positioning the device for preparation of inoculum and for inoculation. Preferably the plate 10 also carries a handle (not shown) located on the plate side opposite the needles 14 to facilitate handling of the plate by a laboratory technician.

The means 11 for preparing and holding the inoculum, and for contacting the inoculating needles with inoculum, is shown as a flat, circular plate or disc having a plurality of depressions or wells 13 for holding the inoculum. In this case, there are 10 wells spaced apart on the plate 11 in circular relationship corresponding to the number and location of the inoculation needles 14 carried by the plate 10. The inoculum holding plate 11 also may include one or more guides (not shown) corresponding to the guides on the inoculation plate for assuring proper alignment with respect thereto.

As will be apparent, the sizes and materials of construction of the plates 10 and 11 may be varied within wide ranges. We have found 3¾ inch diameter thin metal plates to be satisfactory.

In carrying out the invention, the culture dish 12 which is a part of our multiple inoculation system is specially shaped to permit rapid filling of the dish with a solidifiable liquid culture medium, and yet to provide insulation of multiple inoculated samples from one another once the culture medium has solidified, so that migration of microorganisms between compartments is minimized and mutual interference in test reactions is avoided.

To this end, the illustrative culture dish 12 is shown having a flat, circular bottom 15, with an upstanding outer wall 16 secured to the dish bottom and surrounding its periphery. For the purpose of defining a plurality of dish compartments 18, in this case ten compartments corresponding to the ten inoculating needles 14, a plurality of upstanding, inner divider walls 19 are secured to the dish bottom 15 and/or to the outer wall 16, and extend from the outer wall inwardly toward the center of the dish. The number of dish compartments 18 used in carrying out the invention may vary from only two to as many as 20 or more. The compartments in a single dish usually will be, but need not be, uniform in size and shape.

Attention is drawn to the fact that intercommunication means is provided between the dish compartments 18 to permit ready flow of liquid culture medium between compartments. In the drawings, the inner divider walls 19 terminate short of the center of the dish, so that the resulting dish compartments 18 each open toward the center of the dish. As shown, the inner walls 19 are straight and generally radially disposed with respect to the circular dish bottom 15, with the result that the divider walls define a plurality of sector-like (i.e. akin to the sector of an annulus) dish compartments which are in intercommunication with one another in the central portion of the dish. The inner ends 19a of the walls thus define therebetween a plurality of compartment intercommunication openings or interruptions 20 which are relatively narrow in width compared with the average or maximum width of the pie-shaped compartments themselves.

Such limited intercommunication between compartments, i.e. via the relatively small openings 20, is preferred because the openings are sufficient in size to permit solidifiable liquid culture medium poured onto the dish to readily and quickly flow by gravity into, and be retained by, each of the compartments 18; yet once the poured culture medium has solidified, the inner divider walls 19 function to enclose virtually the entirety of the compartments and to thereby isolate them so that adjacent tests will not interfere with one another. The intercommunication means may, of course, take various other forms. For example, the inner walls of the dish could extend all the way to the dish but contain one or more perforations or other type interruptions to permit flow of liquid culture medium therethrough.

The size of the culture dish 12 may be selected as desired, but it will be advantageous to select a size corresponding to that of the inoculation plate 10. The dish 12 may be formed of metal, plastic, or other suitable construction materials. It is preferred to also provide a lid (not shown) sized to fit over and cover the dish when being incubated.

It will be understood, of course, that the shape and configuration of the culture dish 12, and of the compartments 18 therein, may vary as desired. While a circular dish shape has been depicted in the drawings, other shapes may also be used in practicing the invention. For example, the culture dish may have a square, rectangular, or other polygonal shape. In such event, the inner divider walls will extend from the outer, peripheral wall inwardly toward a center line of the rectangle or square. This center line may then be considered to be the center of the dish. The dish also need not have a flat bottom, e.g. a cone shaped bottom may be advantageous in some applications.

In preparing our multiple inoculation system for use, the inoculation needles 14 are sterilized by momentarily holding them in an open flame. Melted agar or other suitable culture medium is poured onto the center or other portion of the culture dish 12 and, as explained above, since the dish compartments 18 are connected at the center of the dish, the medium flows and fills all of the compartments simultaneously to whatever height is desired. The inoculum is prepared by streaking a sample on an appropriate agar plate with an inoculating loop, and incubating the medium. The resulting isolated colonies of organisms are transferred to the separate wells 13 of the holding plate 11, where they are suspended in a sterile broth, saline, water, or other diluent.

When the inoculation needles 14 have cooled, the inoculation plate 10 is superimposed over the holding plate 11 and the needles are inserted into the respective wells 13 containing the inoculum. The needles 14 so charged with the inoculum are then aligned with the respective compartments 18 of the culturing dish 12 and touched to or pressed into the culture medium. Similarly, but without necessarily recharging with the inoculum, the inoculation plate may be used to inoculate as many as 10 to 15 different media contained in separate culturing devices. Finally, the contents of the culture dish 12 are incubated and the growth and biochemical reactions of the organisms on or in the various media are then interpreted to identify the organisms.

One of the advantageous features of the invention is that the inoculation plate 10, inoculum holding plate 11 and culture dish 12 may be sequentially used together as a system, as described above for the identification of an unknown bacterial culture, or they may be used individually for the transferring, cultivation, maintenance, and identification of microorganisms. Utilization of the invention will thus significantly speed up and improve microbiological laboratory procedures. The laboratory technician or microbiologist may now transfer as many as 10 or more cultures at one time, utilize single isolated colonies as the inoculum, and grow 10 or more cultures simultaneously yet in isolation from each other in a single culture dish.

By use of the specially shaped culture dish 12 of the invention, the laboratory technician finds it possible to fill the dish with agar jelly or other liquid culture medium, obtaining an even distribution of jelly in all dish compartments, in a matter of only a few seconds time (e.g. 10 seconds) as compared with 5 or 10 minutes required to fill the individual cups of the "divided Petri dish" used previously. Use of the invention avoids the tedium of prior practices, and minimizes the problems of contamination inherent in time consuming filling of individual cups thereby obviating the need to use specially trained personnel.

Moreover, we find that after inoculation of the culture medium contained in the dish compartments 18 has taken place, the compartments are so well isolated from one another that there is no migration of microorganisms or reaction products from one compartment to another, or at least no such migration for a period long enought (i.e. several days) for the reactions and identifications to have been completed.

Other advantages also inhere in the invention. The three main components 10, 11 and 12 used in carrying out the invention may be wholly or partly disposable or reusable and used aseptically or otherwise. The components are suitable for either manual or mechanically automatic operation.

We claim as our invention:

1. The method of simultaneously cultivating multiple colonies of microorganisms which comprises providing a culture dish having compartments opening into the center portion of the dish, pouring a solidifiable liquid culture medium onto the dish so that the culture medium flows through the center portion of the dish and into each of the dish compartments, allowing the liquid culture medium to solidify, contacting the solidified culture medium in each of the compartments with a colony of microorganisms, and incubating the contents of the culture dish to thereby simultaneously cultivate the multiple colonies of microorganisms.

2. The method of claim 1 in which the liquid culture medium is poured onto the center portion of the culture dish and flows from there into each of the dish compartments.

* * * * *